(12) United States Patent
Huang et al.

(10) Patent No.: US 8,722,207 B2
(45) Date of Patent: May 13, 2014

(54) ORGANOMETALLIC COMPOUND, ORGANIC ELECTROLUMINESCENCE DEVICE AND COMPOSITION EMPLOYING THE SAME

(75) Inventors: Heh-Lung Huang, Yingge Township (TW); Teng-Chih Chao, Pingjhen (TW); Jin-Sheng Lin, Tainan (TW); Hao-Chun Lee, Hsinchu (TW); Mei-Rurng Tseng, Hsinchu (TW)

(73) Assignee: Industrial Technology Research Institute (TW)

( * ) Notice: Subject to any disclaimer, the term of this patent is extended or adjusted under 35 U.S.C. 154(b) by 377 days.

(21) Appl. No.: 13/109,493

(22) Filed: May 17, 2011

(65) Prior Publication Data

US 2011/0285275 A1    Nov. 24, 2011

(30) Foreign Application Priority Data

May 18, 2010    (TW) ................. 99115767 A

(51) Int. Cl.
*H01L 51/54* (2006.01)
*C09K 11/06* (2006.01)

(52) U.S. Cl.
USPC ............ 428/690; 428/917; 546/10; 313/504; 313/506; 252/301.16; 257/40; 257/E51.044

(58) Field of Classification Search
None
See application file for complete search history.

(56) References Cited

U.S. PATENT DOCUMENTS

| 7,445,857 | B2 | 11/2008 | Shen et al. |
| 2003/0068526 | A1 | 4/2003 | Kamatani et al. |
| 2003/0072964 | A1 | 4/2003 | Kwong et al. |
| 2007/0237981 | A1 * | 10/2007 | Shen et al. ................... 428/690 |

FOREIGN PATENT DOCUMENTS

| EP | 1191613 | 3/2002 |
| TW | I242999 | 12/1993 |
| TW | 200623955 | 7/2006 |
| TW | 200900484 | 1/2009 |

OTHER PUBLICATIONS

Lee, Meng-Ting et al., "Host-Free, Yellow Phosphorescent Material in White Organic Light-Emitting Diodes", J. Phys. D: Appl. Phys. 43 (2010) 442003 (4pp).
Huang, Sheng-Yang et al. "Uniform Dispersion of Triplet Emitters in Multi-Layer Solution-Processed Organic Light-Emitting Didoes", Synthetic Metals 160 (2010) 2393-2396.
Office Action dated Jun. 20, 2012 from corresponding German application No. 102011111328.6.

* cited by examiner

*Primary Examiner* — Michael H Wilson
(74) *Attorney, Agent, or Firm* — Lowe Hauptman & Ham, LLP

(57) ABSTRACT

Organometallic compounds and organic electroluminescence devices and compositions employing the same are provided. The organic metal compound has a chemical structure represented by formula (I) or formula (II):

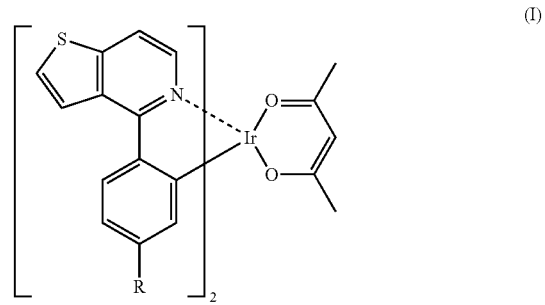

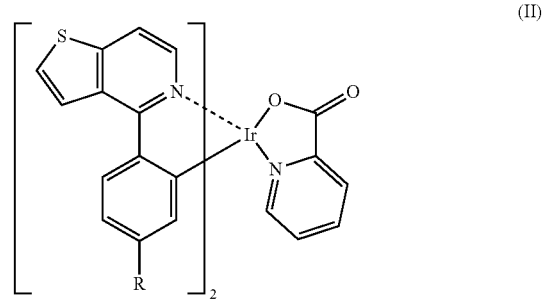

wherein, R is an alkyl group, or cycloalkyl group, such as $C_{1-12}$ alkyl group, or $C_{4-12}$ cycloalkyl group.

10 Claims, 1 Drawing Sheet

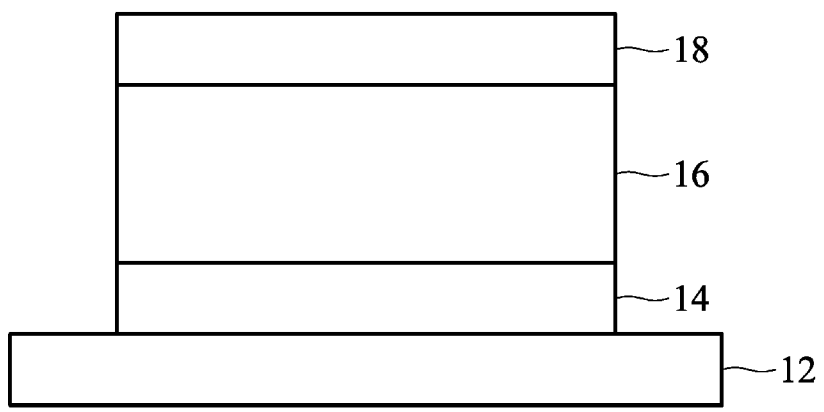

ORGANOMETALLIC COMPOUND, ORGANIC ELECTROLUMINESCENCE DEVICE AND COMPOSITION EMPLOYING THE SAME

CROSS REFERENCE TO RELATED APPLICATIONS

This application is based upon and claims the benefit of priority from the prior Taiwan Patent Application No. 099115767, filed on May 18, 2010, the entire contents of which are incorporated herein by reference.

BACKGROUND

Field

The invention relates to an organometallic compound and organic electroluminescence device employing the same and, more particularly, to an organometallic phosphorescent compound and a phosphorescent organic electroluminescence device employing the same.

Recently, with the development and wide application of electronic products, such as mobile phones, PDAs, and notebook computers, there has been increasing demand for flat display elements which consume less electric power and occupy less space. Organic electroluminescent devices are self-emitting and highly luminous, with wide viewing angles, fast response speeds, and simple fabrication methods, making them an industry display of choice.

Generally, an organic electroluminescent device is composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and hole results in light emission.

Depending on the spin states of the hole and electron, the exciton, which results from the recombination of the hole and electron, can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent material, in order to increase the emissive efficiency of an OLED.

An OLED is typically categorized into a micro-molecular and high-molecular OLED according to the substrate type thereof. A micro-molecular substrate OLED is generally fabricated by way of vacuum evaporation, such that the micro-molecular materials have a good film forming quality. However, 95% of the organic electroluminescent materials are deposited on the chamber wall of the manufacturing equipment used to manufacture the OLED, such that only 5% of the organic electroluminescent materials are coated on a substrate after the manufacturing process, resulting in a high investment cost.

Therefore, a wet process (such as spin coating or blade coating) has been provided to fabricate micro-molecular OLEDs to improve the utilization ratio of organic electroluminescent materials and reduce the cost of manufacturing OLEDs. Unfortunately, conventional phosphorescent organic electroluminescent materials are not suitable to be used in the wet process due to the inferior solubility thereof. Therefore, it is necessary to develop novel phosphorescent organic compounds (especially for orange dopants) suitable for use in a wet process to fabricate phosphorescent OLEDs to solve the above problems.

SUMMARY

An exemplary embodiment of an organometallic compound has a Formula (I) and Formula (II), of:

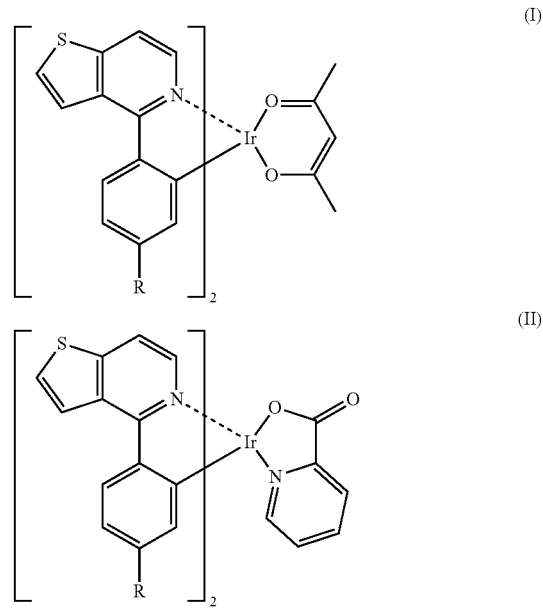

wherein, R is an alkyl group, or cycloalkyl group.

In another exemplary embodiment of the disclosure, an organic electroluminescent device is provided. The device includes a pair of electrodes and an electroluminescent element disposed between the pair of electrodes, wherein the electroluminescent element includes the aforementioned organometallic compound (serving as an orange dopant).

Yet another exemplary embodiment of the disclosure provides a composition including an organic electroluminescent diode host material and the aforementioned organometallic compound (uniformly distributed in a solvent). The organic electroluminescent diode host material can include polymer material such as poly(vinylcarbazole) (PVK). Further, the composition can include a carrier promoter (such as electron promoter (including PBD(2-(4-biphenyl)-5-(4-tert-butylphenyl)-1,3,4-oxadiazole)) or hole promoter (including TPD(N, N'-diphenyl-N,N'-(bis(3-methylphenyl)-[1,1-biphenyl]-4, 4'diamine)).

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 1 shows a cross section of an organic electroluminescent device disclosed by an embodiment of the disclosure.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

The disclosure provides an organometallic compound prepared by introducing an alkyl group or cycloalkyl group to bond with a 4-phenylthieno[3,2-c]pyridine moiety, in order to increase the solubility thereof. For example, a short-chain alkyl group (such as methyl or ethyl) can be boned onto a 4-phenylthieno[3,2-c]pyridine moiety, and the obtained organometallic compound would be suitable for use in a wet process or evaporation process. On the other hand, a long-chain alkyl group (such as tert-butyl or cyclohexyl) can be boned onto a 4-phenylthieno[3,2-c]pyridine moiety, and the obtained organometallic compound would be suitable for use in a wet process. Moreover, the organometallic compound of the disclosure can be applied in an organic electroluminescent device for enhancing the efficiency thereof.

Organometallic Compound

The disclosure provides an organometallic compound having a structure represented by Formula (I) or Formula (II):

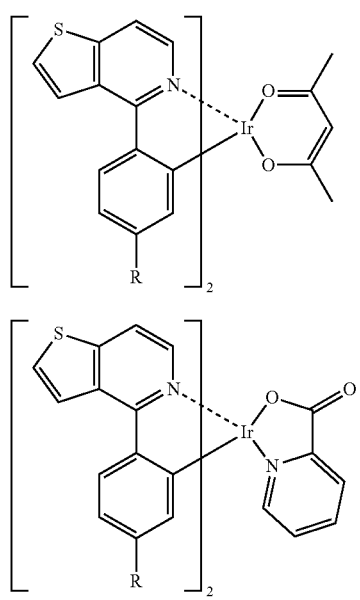

wherein, R is an alkyl group, or cycloalkyl group. For example, R can be $C_{1-12}$ alkyl group, or $C_{4-12}$ cycloalkyl group, such as methyl, ethyl, propyl, iso-propyl, butyl, iso-butyl, sec-butyl, tert-butyl, pentyl, sec-pentyl, cyclopentyl, hexyl, cyclohexyl, heptyl, octyl, nonyl, decyl, hendecyl, or dodecyl.

The following examples are intended to illustrate the invention more fully without limiting the scope, since numerous modifications and variations will be apparent to those skilled in this art.

EXAMPLE 1

Preparation of Compound PO-01-M 7.0 g of compound (1) (2-(2-aminoethyl)thiophene, 55.1 mmole) and 200 mL of $H_2O$ were added in a 500 mL reaction bottle. Next, 11.0 mL of compound (2) (p-toluoyl chloride, 82.7 mmole) was added dropwise into the reaction bottle at 0° C. After, an NaOH aqueous solution (20%) was added into the reaction bottle and stirred overnight. After filtration, a compound (3) (white solid) was obtained with a yield of 93%. The synthesis pathway of the above reaction was as follows:

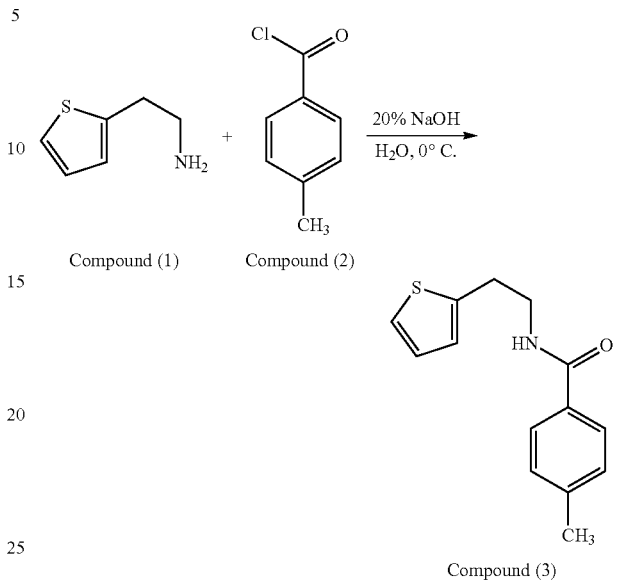

Next, 5.0 g of compound (3) (20.4 mmole) and 80 mL of toluene were added into a 250 mL reaction bottle. Next, 5.7 mL of POCl3 (61.2 mmole) was added dropwise into the reaction bottle at 0° C. After stiffing and refluxing for 2 hr, a saturated $NaHCO_3$ aqueous solution was added into the reaction bottle for quenching the reaction. After toluene extraction, an organic layer was collected and dried by magnesium sulfate. After concentration, a compound (4) (crystal) was obtained with a yield of 50%. The synthesis pathway of the above reaction was as follows:

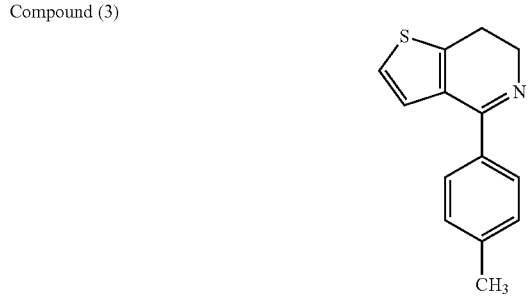

Next, 3.0 g of compound (4) (13.2 mmole), 3.0 g of Pd/C (10%), and 100 mL of toluene was added into a 250 ml reaction bottle. After refluxing for 18 hr, the result was filtrated by Celite 545 to remove Pd/C. After concentrating the filtrate, a compound (5) was obtained with a yield of 85%. The synthesis pathway of the above reaction was as follows:

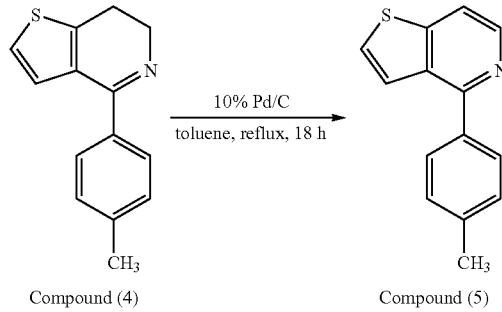

Compound (4)        Compound (5)

Next, 5.0 g of compound (5) (22.2 mmole), 3.0 g of $IrCl_3 \cdot x H_2O$ (10 mmole), 15 mL of 2-methoxy ethanol, and 5 mL of water was added into a 100 mL reaction bottle. After reacting for 24 hr, the reaction was quenched by water. After filtration, a compound (6) (orange solid) was obtained with a yield of 49%. The synthesis pathway of the above reaction was as follows:

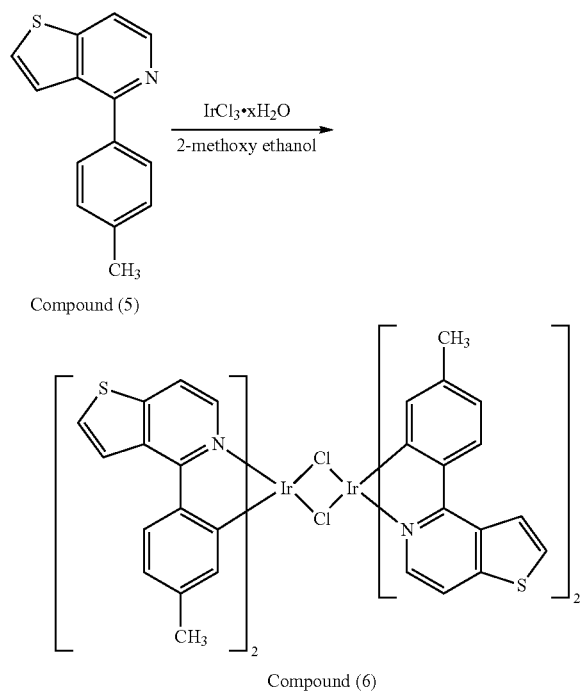

Compound (5)

Compound (6)

3.3 g of compound (6) (4.0 mmole), 1.65 g of acac (acetyl acetone, 16 mmole), 1.71 g of Na2CO3 (16 mmole), and 40 mL of 2-methoxy ethanol were added into a 100 mL reaction bottle. After refluxing for 24 hr and cooling, 40 mL of water was added into the reaction bottle. After filtration and purification by column chromatography with methylene dichloride, a compound PO-01-M (orange powder) was obtained with a yield of 50%. The synthesis pathway of the above reaction was as follows:

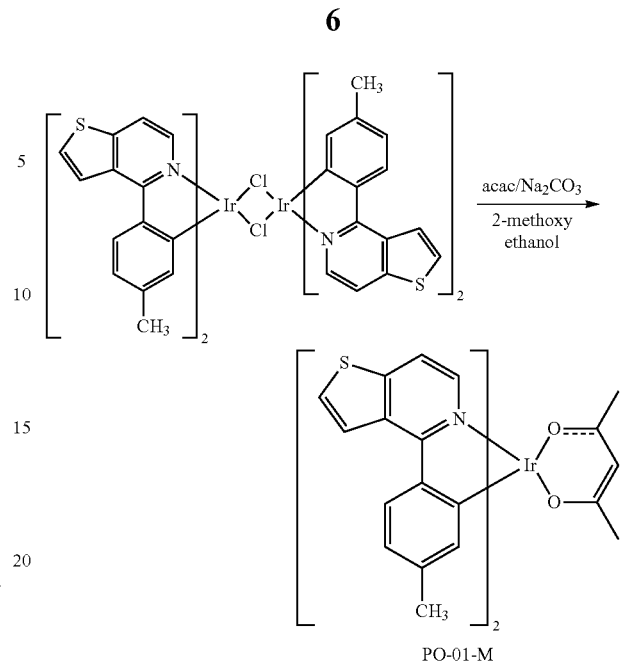

PO-01-M

The physical measurement of the compound PO-01-M is listed below:

$^1$H NMR (CDCl3, 200 MHz) δ 8.41 (d, J=3.4 Hz, 2H), 8.34 (d, J=5.6 Hz, 2H), 8.02 (d, J=8.0 Hz, 2H), 7.66 (d, J=5.6 Hz, 2H), 7.60 (d, J=6.2 Hz, 2H), 6.69 (d, J=7.6 Hz, 2H), 6.15 (s, 2H), 5.18 (s, 1H), 2.03 (s, 6H), 1.75 (s, 6H).

EXAMPLE 2

Preparation of Compound PO-01-TB 7.0 g of compound 1 (2-(2-aminoethyl)thiophene, 55.1 mmole) and 200 mL of $H_2O$ were added into a 500 mL reaction bottle. Next, 16.2 g of compound (7) (4-t-butyl benzoyl chloride, 82.5 mmole) was added dropwise into the reaction bottle at 0° C. After, an NaOH aqueous solution (20%) was added into the reaction bottle and stirred overnight. After filtration, a compound (8) (white solid) was obtained with a yield of 98%. The synthesis pathway of the above reaction was as follows:

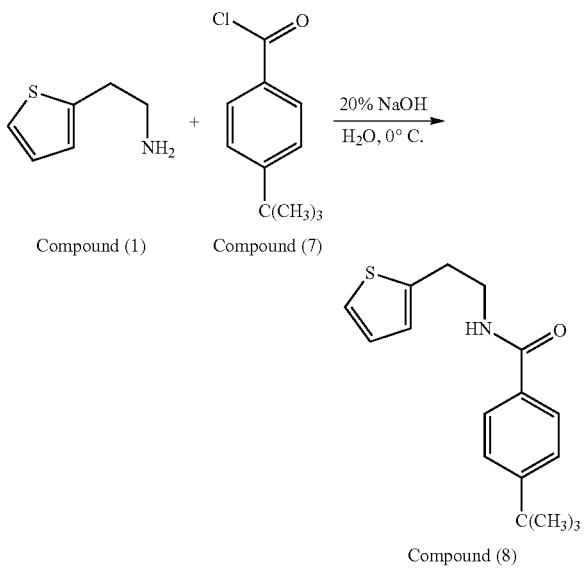

Compound (1)        Compound (7)

Compound (8)

Next, 2.87 g of compound (8) (10 mmole) and 80 mL of toluene were added into a 250 mL reaction bottle. Next, 2.8 mL of POCl$_3$ (61.2 mmole) was added dropwise into the reaction bottle at 0° C. After stiffing and refluxing for 2 hr, a saturated NaHCO$_3$ aqueous solution was added into the reaction bottle for quenching the reaction. After toluene extraction, an organic layer was collected and dried by magnesium sulfate. After concentration, a compound (9) (crystal) was obtained with a yield of 60%. The synthesis pathway of the above reaction was as follows:

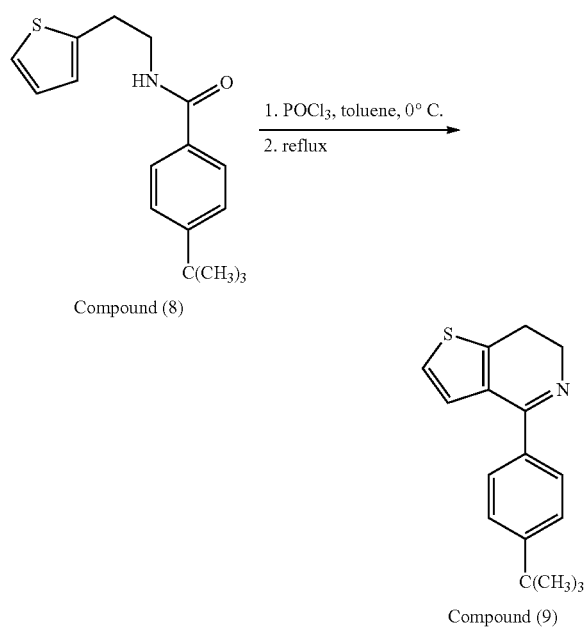

Next, 2.7 g of compound (9) (10 mmole), 0.5 g of Pd/C (10%), and 100 mL of toluene was added into a 250 ml reaction bottle. After refluxing for 18 hr, the result was filtrated by Celite 545 to remove Pd/C. After concentrating the filtrate and purification by column chromatography with ethyl acetate and hexane (1:9), a compound (10) was obtained with a yield of 79%. The synthesis pathway of the above reaction was as follows:

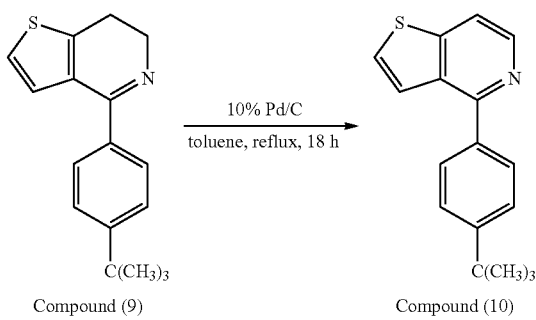 [SMILES: CC(C)(C)c1ccc(C2=NCCc3sccc32)cc1 ; CC(C)(C)c1ccc(-c2nccc3sccc23)cc1]

Next, 5.0 g of compound (10) (18.7 mmole), 2.9 g of IrCl$_3$.x H$_2$O (8.5 mmole), 15 mL of 2-methoxy ethanol, and 5 mL of water was added into a 100 mL reaction bottle. After reacting for 24 hr, the reaction was quenched by water. After filtration, a compound (11) (orange solid) was obtained with a yield of 49%. The synthesis pathway of the above reaction was as follows:

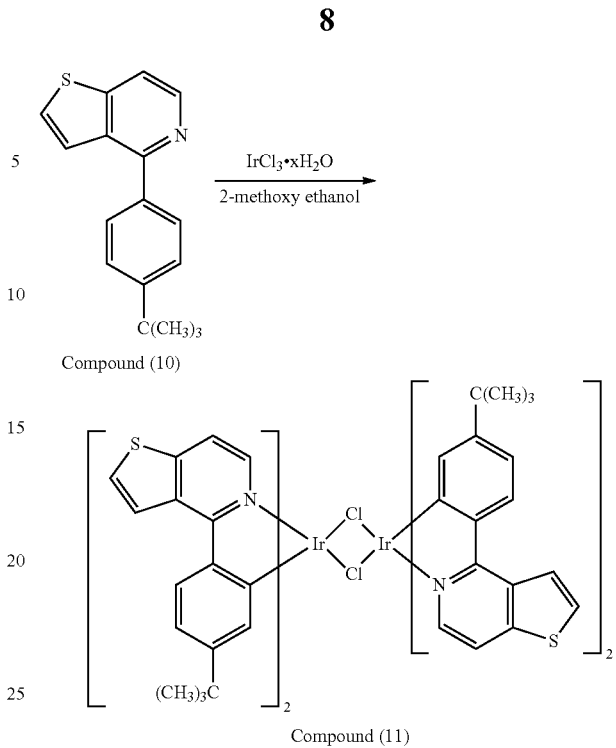

1.48 g of compound (6) (1.5 mmole), 0.6 g of acac (acetyl acetone, 6 mmole), 0.64 g of Na2CO3 (6 mmole), and 15 mL of 2-methoxy ethanol were added into a 100 mL reaction bottle. After refluxing for 24 hr and cooling, 40 mL of water was added into the reaction bottle. After filtration and purification by column chromatography with methylene dichloride, a compound PO-01-TB (orange powder) was obtained with a yield of 89%.

The synthesis pathway of the above reaction was as follows:

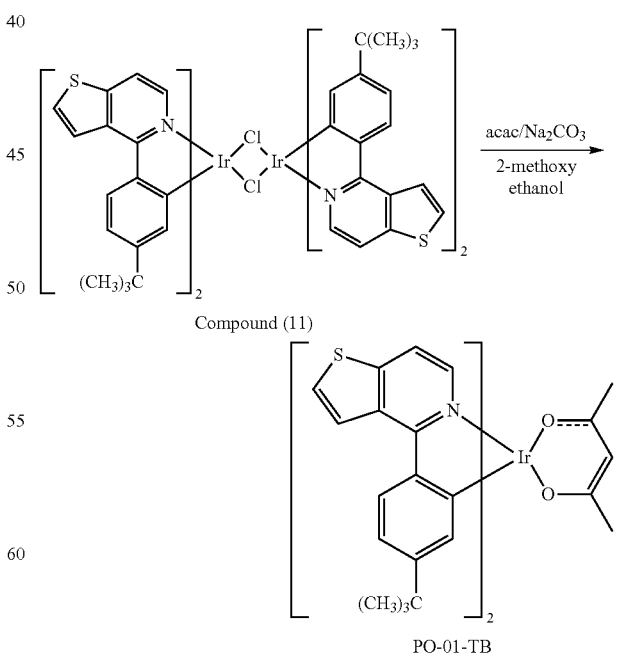

Physical measurement of the compound PO-01-TB is listed below:

$^1$H NMR (CDCl3, 200 MHz) δ 8.45 (d, J=6.6 Hz, 2H), 8.30 (d, J=5.4 Hz, 2H), 7.99 (d, J=8.4 Hz, 2H), 7.64 (d, J=5.0 Hz, 4H), 6.88 (dd, J=8.6, 1.8 Hz, 2H), 6.22 (d, J=1.8 Hz, 2H), 5.22 (s, 1H), 1.79 (s, 6H), 0.98 (s, 18H).

EXAMPLE 3

Preparation of Compound PO-01-HEX 9.4 g of compound (1) (2-(2-aminoethyl)thiophene, 74.1 mmole) and 200 mL of H$_2$O were added in a 500 mL reaction bottle. Next, 25.0 g of compound (12) (4-n-hexyl benzoyl chloride, 111.2 mmole) was added dropwise into the reaction bottle at 0° C. After, an NaOH aqueous solution (20%) was added into the reaction bottle and stirred overnight. After filtration, a compound (13) (white solid) was obtained with a yield of 88%. The synthesis pathway of the above reaction was as follows:

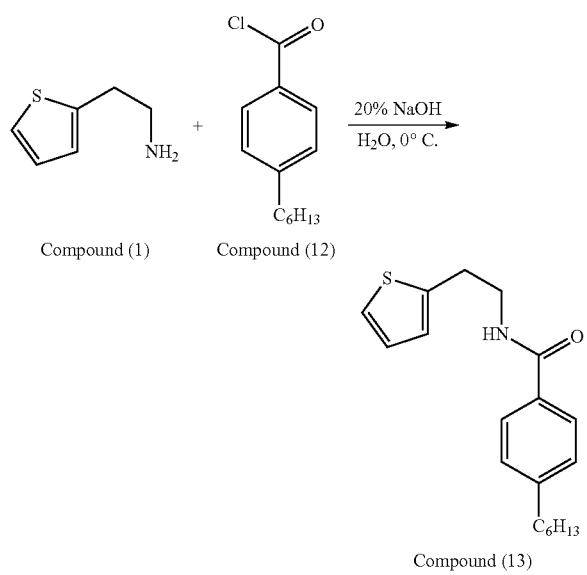

Next, 5.0 g of compound (13) (15.9 mmole) and 80 mL of toluene were added into a 250 mL reaction bottle. Next, 4.4 mL of POCl3 (47.6 mmole) was added dropwise into the reaction bottle at 0° C. After stiffing and refluxing for 2 hr, a saturated NaHCO$_3$ aqueous solution was added into the reaction bottle for quenching the reaction. After toluene extraction, an organic layer was collected and dried by magnesium sulfate. After concentration, a compound (14) (crystal) was obtained with a yield of 55%. The synthesis pathway of the above reaction was as follows:

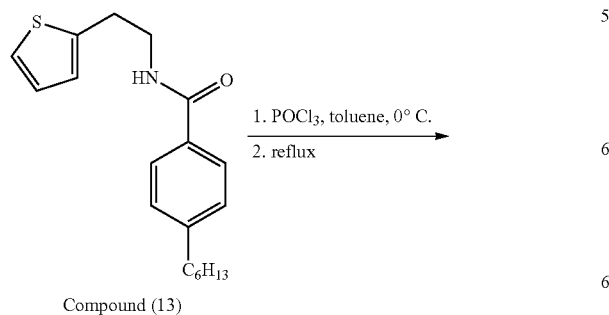

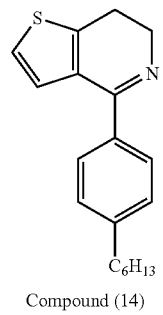

Compound (14)

Next, 3.0 g of compound (14) (13.2 mmole), 3.0 g of Pd/C (10%), and 100 mL of toluene was added into a 250 ml reaction bottle. After refluxing for 18 hr, the result was filtrated by Celite 545 to remove Pd/C. After concentrating the filtrate and purification by column chromatography with ethyl acetate and hexane (1:9), a compound (15) was obtained with a yield of 75%. The synthesis pathway of the above reaction was as follows:

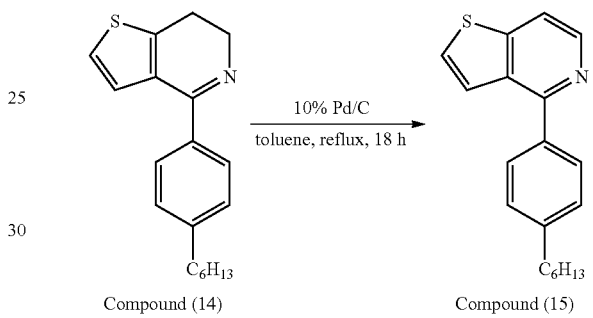

Next, 3.8 g of compound (5) (12.88 mmole), 1.7 g of IrCl$_3$.x H$_2$O (5.85 mmole), 15 mL of 2-methoxy ethanol, and 5 mL of water was added into a 100 mL reaction bottle. After reacting for 24 hr, the reaction was quenched by water. After filtration, a compound (16) (orange solid) was obtained with a yield of 40%. The synthesis pathway of the above reaction was as follows:

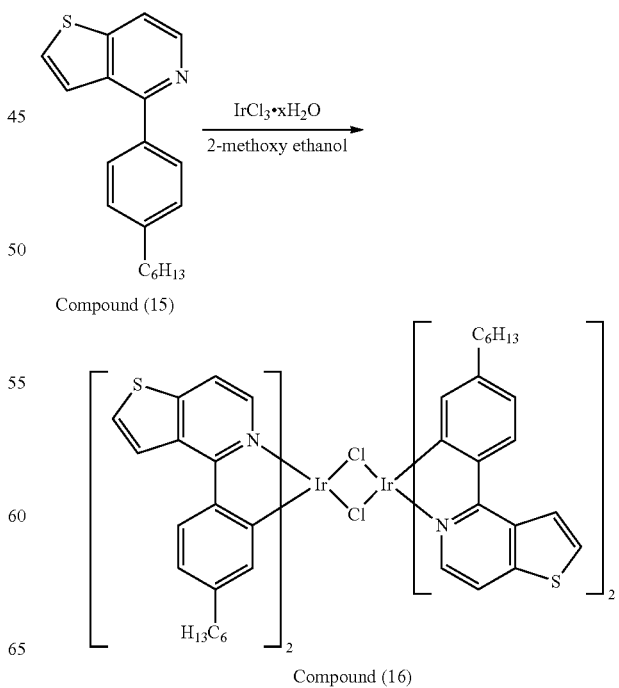

5.0 g of compound (6) (4.0 mmole), 1.23 g of acac (acetyl acetone, 12.26 mmole), 1.30 g of Na2CO3 (12.26 mmole), and 30 mL of 2-methoxy ethanol were added into a 100 mL reaction bottle. After refluxing for 24 hr and cooling, 40 mL of water was added into the reaction bottle. After filtration and purification by column chromatography with methylene dichloride and hexane (1:3), a compound PO-01-HEX (orange powder) was obtained with a yield of 63%. The synthesis pathway of the above reaction was as follows:

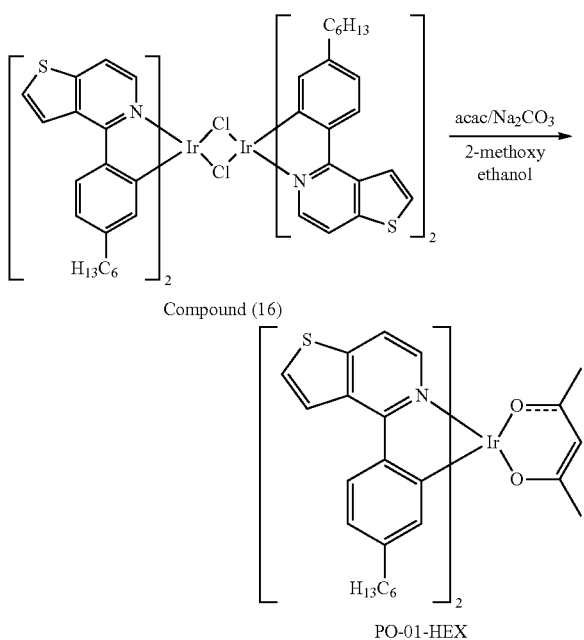

Physical measurement of the compound PO-01-HEX is listed below:

$^1$H NMR (CDCl3, 200 MHz) δ 8.42 (d, J=3.4 Hz, 2H), 8.32 (d, J=5.0 Hz, 2H), 8.01 (d, J=5.0 Hz, 2H), 7.65 (d, J=5.4 Hz, 2H), 7.42 (d, J=4.8 Hz, 2H), 6.69 (d, J=7.6 Hz, 2H), 6.10 (s, 2H), 5.19 (s, 1H), 2.26 (t, J=6.6 Hz, 4H), 1.76 (s, 6H), 1.55 (s, 4H), 1.10 (br, 12H), 0.80 (t, J=7.2 Hz, 6H).

EXAMPLE 4

Solubility Test

The compound PO-01-TB (Example 2), the compound PO-01-HEX (Example 3), and a compound PO-01 (having a structure of

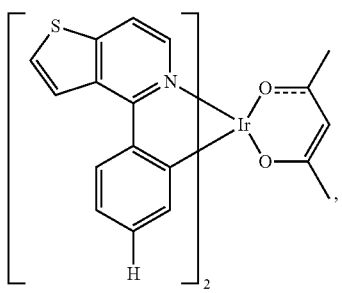

serving as a control group) were respectively dissolved in chlorobenzene to prepare 0.5%, 0.8%, 1%, 1.5%, 2%, and 3% organometallic compound solutions, and the soluble degree of the organometallic compounds were observed. The results are shown in Table 1:

TABLE 1

|           | 3% | 2% | 1.5% | 1% | 0.8% | 0.5%                     |
|-----------|----|----|------|----|------|--------------------------|
| PO-01     | X  | X  | X    | X  | X    | ○ (approximately dissolved) |
| PO-01-TB  | X  | X  | ○    | ○  | ○    | ○                        |
| PO-01-HEX | ○  | ○  | ○    | ○  | ○    | ○                        |

(X: indissolvable or partially dissolvable, ○: completely dissolvable)

As shown in Table 1, the organometallic compounds having 4-phenylthieno[3,2-c]pyridine moiety bonded with a long-chain alkyl group or cycloalkyl group (such as PO-01-TB and PO-01-HE) exhibited improved solubility (of more than 1.5% in chlorobenzene) in comparison with compound PO-01 (R is H, having a solubility of 0.5% in chlorobenzene).

Organic Electroluminescent Device

FIG. 1 shows an embodiment of an organic electroluminescent device 10. The electroluminescent device 100 includes a substrate 12, a bottom electrode 14, an electroluminescent element 16, and a top electrode 18, as shown in FIG. 1. The organic electroluminescent device can be top-emission, bottom-emission, or dual-emission devices.

The substrate 12 can be a glass plastic, or semiconductor substrate. Suitable materials for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Further, at least one of the bottom and top electrodes 14 and 18 is transparent.

The electroluminescent element 16 at least includes an emission layer, and can further include a hole injection layer, a hole transport layer, an electron transport layer, and an electron injection layer. In an embodiment of the disclosure, at least one layer of the electroluminescent element 16 includes the aforementioned organometallic compound.

According to an embodiment of the disclosure, the organic electroluminescent device can be a phosphorescent organic electroluminescent device, and the phosphorescent organic electroluminescent device can include an emission layer including a host material and a phosphorescent dopant, wherein the host material includes the aforementioned organometallic compounds.

In order to clearly disclose the organic electroluminescent devices of the disclosure, the following examples (employing the organometallic compounds of Examples 1-3 and evaporation or wet processes) and comparative examples are intended to illustrate the disclosure more fully without limiting their scope, since numerous modifications and variations will be apparent to those skilled in this art.

Dry Process

COMPARATIVE EXAMPLE 1

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, NPB(N,N'-di(naphthalene-1-yl)-N,N'-diphenyl-benzidine, with a thickness of 30 nm), CBP(4, 4'-N,N'-dicarbazole-biphenyl) doped with PO-01 (

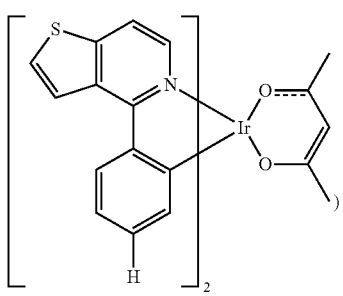

(the ratio between CBP and PO-01 was 100:6, with a thickness of 30 nm), with a thickness of 30 nm), BCP (2,9-dimethyl-4,7diphenyl-1,10-phenanthroline, with a thickness of 10 nm), Alq3(tris (8-hydroxyquinoline) aluminum, with a thickness of 20 nm), LiF (with a thickness of 0.5 nm), and Al (with a thickness of 120 nm) were subsequently formed on the ITO film at 10-6 Pa, obtaining the electroluminescent device (1). The materials and layers formed therefrom are described in the following:

ITO/NPB/CBP:PO-01 (6%)/BCP/Alq3/LiF/Al

The optical properties of the electroluminescent device (1), as described in Comparative Example 1, were measured by a PR650 (purchased from Photo Research Inc.) and a Minolta TS110. The results are shown in Table 2.

EXAMPLE 5

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, NPB(N,N'-di(naphthalene-1-yl)-N,N'-diphenyl-benzidine, with a thickness of 30 nm), CBP(4,4'-N,N'-dicarbazole-biphenyl) doped with PO-01 (

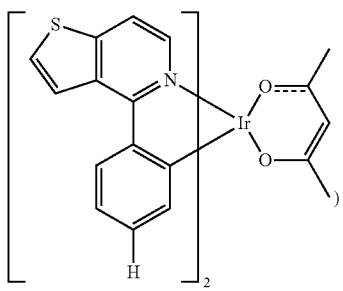

(the ratio between CBP and PO-01-TB was 100:6, with a thickness of 30 nm), with a thickness of 30 nm), BCP (2,9-dimethyl-4,7diphenyl-1,10-phenanthroline, with a thickness of 10 nm), Alq3(tris (8-hydroxyquinoline) aluminum, with a thickness of 20 nm), LiF (with a thickness of 0.5 nm), and Al (with a thickness of 120 nm) were subsequently formed on the ITO film at 10-6 Pa, obtaining the electroluminescent device (2). The materials and layers formed therefrom are described in the following:

ITO/NPB/CBP:PO-01-TB (6%)/BCP/Alq3/LiF/Al

The optical properties of the electroluminescent device (2), as described in Example 5, were measured by a PR650 (purchased from Photo Research Inc.) and a Minolta TS110. The results are shown in Table 2.

TABLE 2

| | Driving voltage (v) | current efficiency (cd/A) | CIE (X, Y) | Wavelength (nm) |
|---|---|---|---|---|
| electroluminescent device (1) | 5.2 | 40.3 | (0.48, 0.50) | 560 |
| electroluminescent device (2) | 4.1 | 62.8 | (0.48, 0.51) | 560 |

As shown in Table 2, with the premise that the same host material was used, the organometallic compound PO-01-TB of the disclosure showed superior efficiency and reduced voltage in comparison with the compound PO-01 of the Comparative Example 1.

Wet Process

COMPARATIVE EXAMPLE 2

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, PEDOT(poly(3,4)-ethylendioxythiophen):PSS(e-polystyrenesulfonate) was coated on the ITO film by a blade and spin coating process (with a rotation rate of 4000 rpm) and baked at 100° C. for 40 min to form a PEDO:PSS film (with a thickness of 50 nm, serving as a hole-inject layer). Next, TFB (poly[99,9-dioctylfluorenyl-2,7-diyl)-co-(4,4'-(N-(4-s-butylphenyl))diphenylamine)]) was coated on the PEDO:PSS film by a blade coating process and baked at 100° C. for 40 min to form a TFB film (with a thickness of 20 nm, serving as a hole-transport layer). Next, a composition including PVK(poly(vinylcarbazole)), PBD(2-(4-biphenyl)-5-(4-tert-butylphenyl)-1,3,4-oxadiazole), TPD (N,N'-diphenyl-N,N'-(bis(3-methylphenyl)-[1,1-biphenyl]-4,4'diamine)), and PO-01 (the weight ratio of PVK:PBD:TPD:PO-01 is 55:34:9:6, dissolved in chlorobenzene) was coated on the TFB film by a blade and spin coating process to form a light emitting film (with a thickness of 30 nm). Next, TPBI(1,3,5-tris(phenyl-2-benzimidazolyl)-benzene) was coated on the PEDO:PSS film by a blade and spin coating process and baked at 100° C. for 40 min to form a TPBI film (with a thickness of 20 nm, serving as a hole-block/electron-transport layer). Next, LiF (with a thickness of 0.5 nm), and Al (with a thickness of 120 nm) were subsequently formed on the TPBI film at 10-6 Pa, obtaining the electroluminescent device (3). The materials and layers formed therefrom are described in the following:

ITO/PEDOT(CH8000)/TEB/PVK:PBD:TPD:PO-01/TPBI/LiF/Al

The optical properties of the electroluminescent device (3), as described in Comparative Example 2, were measured by a PR650 (purchased from Photo Research Inc.) and a Minolta TS110. The results are shown in Table 3.

EXAMPLE 6

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, PEDOT(poly(3,4)-ethylendioxythiophen):PSS(e-polystyrenesulfonate) was coated on the ITO film by a blade and spin coating process (with a rotation rate of 4000 rpm) and baked at 100° C. for 40 min to form a PEDO:PSS film (with a thickness of 50 nm, serving as a hole-inject layer). Next, TFB (poly[99,9-dioctylfluorenyl-2,7-diyl)-co-(4,4'-(N-(4-s-butylphenyl))diphenylamine)]) was coated on the PEDO:PSS film by a blade coating process and baked at 100° C. for 40 min to form a TFB film (with a thickness of 20 nm, serving as a hole-transport layer). Next, a composition including PVK(poly(vinylcarbazole)), PBD(2-(4-biphenyl)-5-(4-tert-butylphenyl)-1,3,4-oxadiazole), TPD (N,N'-diphenyl-N,N'-(bis(3-methylphenyl)-[1,1-biphenyl]-4,4'diamine)), and PO-01-TB (the weight ratio of PVK:PBD:TPD:PO-01-TB is 61:24:9:6, dissolved in chlorobenzene) was coated on the TFB film by a blade and spin coating process to form a light emitting film (with a thickness of 30 nm). Next, TPBI(1,3,5-tris(phenyl-2-benzimidazolyl)-benzene) was coated on the PEDO:PSS film by a blade and spin coating process and baked at 100° C. for 40 min to form a TPBI film (with a thickness of 20 nm, serving as a hole-block/electron-transport layer). Next, LiF (with a thickness of 0.5 nm), and Al (with a thickness of 120 nm) were subsequently formed on the TPBI film at 10-6 Pa, obtaining the electroluminescent device (4). The materials and layers formed therefrom are described in the following:

ITO/PEDOT(CH8000)/TEB/PVK:PBD:TPD:PO-01-TB/TPBI/LiF/Al

The optical properties of the electroluminescent device (4), as described in Example 6, were measured by a PR650 (purchased from Photo Research Inc.) and a Minolta TS110. The results are shown in Table 3.

EXAMPLE 7

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, PEDOT(poly(3,4)-ethylendioxythiophen):PSS(e-polystyrenesulfonate) was coated on the ITO film by a blade and spin coating process (with a rotation rate of 4000 rpm) and baked at 100° C. for 40 min to form a PEDO:PSS film (with a thickness of 50 nm, serving as a hole-inject layer). Next, TFB (poly[99,9-dioctylfluorenyl-2,7-diyl)-co-(4,4'-(N-(4-s-butylphenyl))diphenylamine)]) was coated on the PEDO:PSS film by a blade coating process and baked at 100° C. for 40 min to form a TFB film (with a thickness of 20 nm, serving as a hole-transport layer). Next, a composition including PVK(poly(vinylcarbazole)), PBD(2-(4-biphenyl)-5-(4-tert-butylphenyl)-1,3,4-oxadiazole), TPD (N,N'-diphenyl-N,N'-(bis(3-methylphenyl)-[1,1-biphenyl]-4,4'diamine)), and PO-01-HEX (the weight ratio of PVK:PBD:TPD:PO-01-HEX is 61:24:9:6, dissolved in chlorobenzene) was coated on the TFB film by a blade and spin coating process to form a light emitting film (with a thickness of 30 nm). Next, TPBI(1,3,5-tris(phenyl-2-benzimidazolyl)-benzene) was coated on the PEDO:PSS film by a blade and spin coating process and baked at 100° C. for 40 min to form a TPBI film (with a thickness of 20 nm, serving as a hole-block/electron-transport layer). Next, LiF (with a thickness of 0.5 nm), and Al (with a thickness of 120 nm) were subsequently formed on the TPBI film at 10-6 Pa, obtaining the electroluminescent device (5). The materials and layers formed therefrom are described in the following.

ITO/PEDOT(CH8000)/TEB/PVK:PBD:TPD:PO-01-HEX/TPBI/LiF/Al

The optical properties of the electroluminescent device (5), as described in Example 7, were measured by a PR650 (purchased from Photo Research Inc.) and a Minolta TS110. The results are shown in Table 3.

TABLE 3

| | efficiency (cd/A) | CIE (x, y) | wavelength (nm) |
|---|---|---|---|
| electroluminescent device (3) | 2.7 | (0.49, 0.50) | 560 |
| electroluminescent device (4) | 35 | (0.48, 0.51) | 560 |
| electroluminescent device (5) | 20 | (0.47, 0.52) | 558 |

As shown in Table 3, with the premise that the same host material and wet process were used, the organometallic compound PO-01-Tb and PO-01-HEX of the disclosure showed superior efficiency in comparison with the compound PO-01 of the Comparative Example 2 due to the improved solubility.

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organometallic compound having a Formula (I) or Formula (II), of:

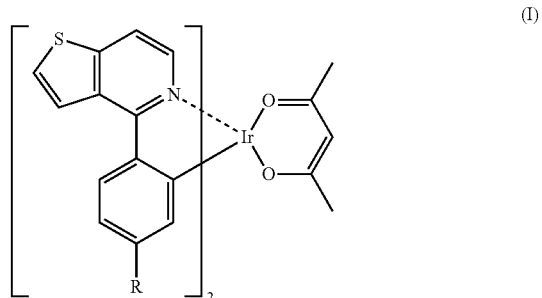

(I)

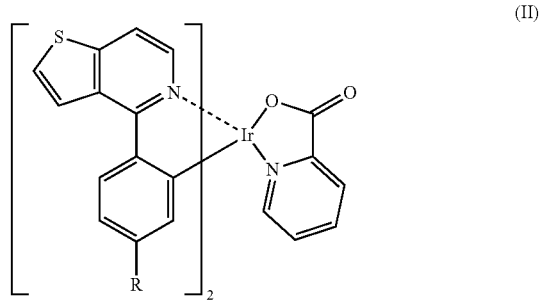

(II)

wherein, R is an alkyl group, or cycloalkyl group.

2. The organometallic compound as claimed in claim 1, wherein R is $C_{1-12}$ alkyl group, or $C_{4-12}$ cycloalkyl group.

3. The organometallic compound as claimed in claim 1, wherein R is a methyl, ethyl, propyl, iso-propyl, butyl, iso-butyl, sec-butyl, tert-butyl, pentyl, sec-pentyl, cyclopentyl, hexyl, cyclohexyl, heptyl, octyl, nonyl, decyl, hendecyl, or dodecyl.

4. An organic electroluminescence device, comprising:
a pair of electrodes; and
an electroluminescent element disposed between the pair of electrodes, wherein the electroluminescent element comprises the organometallic compound having a Formula (I) or (II),

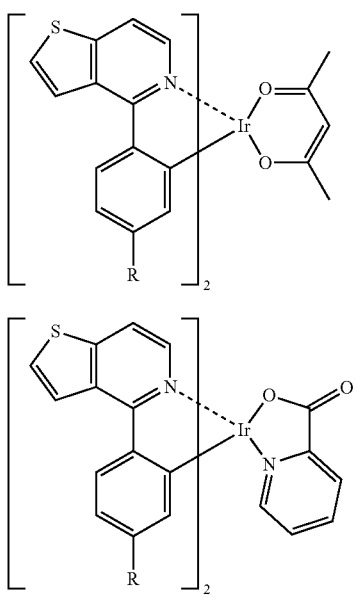

wherein, R is an alkyl group, or cycloalkyl group.

5. The organic electroluminescence device as claimed in claim 4, wherein R is a $C_{1-12}$ alkyl group, or $C_{4-12}$ cycloalkyl group.

6. The organic electroluminescence device as claimed in claim 4, wherein R is a methyl, ethyl, propyl, iso-propyl, butyl, iso-butyl, sec-butyl, tert-butyl, pentyl, sec-pentyl, cyclopentyl, hexyl, cyclohexyl, heptyl, octyl, nonyl, decyl, hendecyl, or dodecyl.

7. The organic electroluminescence device as claimed in claim 4, wherein the electroluminescent element is fabricated by an evaporation process.

8. The organic electroluminescence device as claimed in claim 4, wherein the electroluminescent element is fabricated by a wet process.

9. The organic electroluminescence device as claimed in claim 4, wherein the electroluminescent element emits orange light under a bias voltage 10. A composition, comprising:
 an organic electroluminescent host material; and
 an organometallic compound having a Formula (I) or (II),

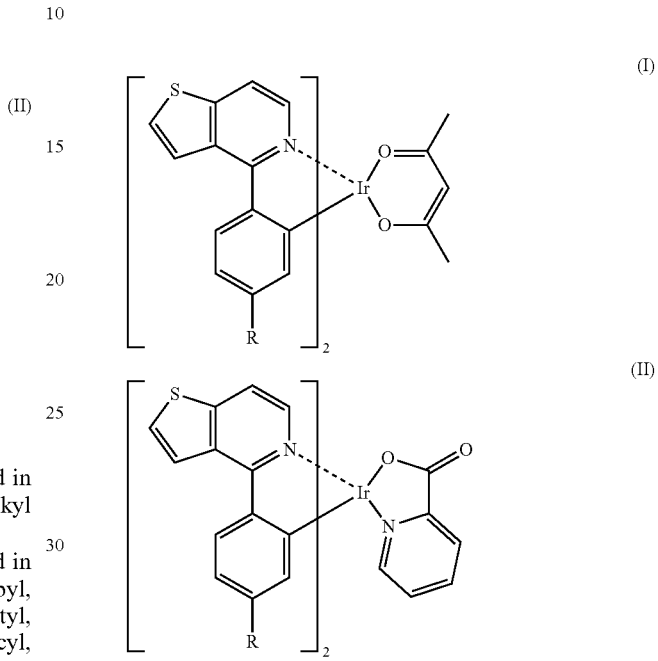

wherein, R is an alkyl group, or cycloalkyl group.

* * * * *